United States Patent
Kaharu et al.

(10) Patent No.: US 7,601,339 B2
(45) Date of Patent: Oct. 13, 2009

(54) HAIR COSMETIC COMPOSITION

(75) Inventors: Takeshi Kaharu, Wakayama (JP); Katsuhisa Inoue, Wakayama (JP)

(73) Assignee: Kao Corporation, Tokyo (JP)

( * ) Notice: Subject to any disclaimer, the term of this patent is extended or adjusted under 35 U.S.C. 154(b) by 668 days.

(21) Appl. No.: 11/098,528

(22) Filed: Apr. 5, 2005

(65) Prior Publication Data

US 2005/0232893 A1    Oct. 20, 2005

(30) Foreign Application Priority Data

Apr. 15, 2004    (JP) .............................. 2004-120515

(51) Int. Cl.
*A61Q 5/12* (2006.01)
(52) U.S. Cl. .................................. 424/70.27
(58) Field of Classification Search ........................ None
See application file for complete search history.

(56) References Cited

U.S. PATENT DOCUMENTS

| 2003/0012761 A1 * | 1/2003 | Yoshida et al. ........... 424/70.17 |
| 2004/0096412 A1 | 5/2004 | Uehara et al. |

FOREIGN PATENT DOCUMENTS

| JP | 05-271035 | 10/1993 |
| JP | 5-271035 | 10/1993 |
| JP | 09-071515 | 3/1997 |
| JP | 9-71515 | 3/1997 |
| JP | 11-79947 | 3/1999 |
| JP | 11-079947 | 3/1999 |
| JP | 2000-053537 | 2/2000 |
| JP | 2000-53537 | 2/2000 |
| JP | 2000-501430 | 2/2000 |
| JP | 2001-342116 | 12/2001 |
| JP | 2002-500173 | 1/2002 |
| JP | 2002-114648 | 4/2002 |
| JP | 2003-183136 | 7/2003 |
| WO | WO 98/40046 | 9/1998 |
| WO | WO 99/34768 | 7/1999 |
| WO | WO 2004/030646 A1 | 4/2004 |

OTHER PUBLICATIONS

"Fragrance Journal", vol. 24, No. 12, 1996, pp. 106-111 (with partial English translation and English Abstract).
Patent Abstracts of Japan, JP 2002-114648, Apr. 16, 2002.
U.S. Appl. No. 11/911,011, filed Oct. 9, 2007, Kaharu.

* cited by examiner

*Primary Examiner*—M P Woodward
*Assistant Examiner*—Bethany Barham
(74) *Attorney, Agent, or Firm*—Oblon, Spivak, McClelland, Maier & Neustadt, L.L.P.

(57) ABSTRACT

The invention relates to a hair cosmetic composition comprising amideamine (I) and aliphatic alcohol (II):

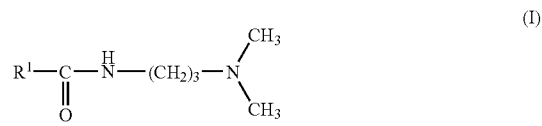

wherein $R^1CO$ represents aliphatic acid residues among which C20 or more aliphatic acid residues account for 60 wt % or more, preferably 75 wt % or more, C20 aliphatic acid residues account for 3 wt % or more, and C22 aliphatic acid residues account for 50 to 95 wt %, and $$R^2-OH \qquad (II)$$

wherein $R^2$ represents C8 to C30 aliphatic hydrocarbon groups wherein linear aliphatic hydrocarbon groups account for 80 wt % or more to the total aliphatic hydrocarbon groups.

20 Claims, No Drawings

HAIR COSMETIC COMPOSITION

FIELD OF THE INVENTION

The present invention relates to a hair cosmetic composition.

BACKGROUND OF THE INVENTION

Hair cosmetics such as a rinse, conditioner, treatment etc. are used for improving the feel of hair after shampooing. These hair cosmetics are used mainly in the form of a gelled emulsion after incorporation of a quaternary ammonium salt as a main component to improve the feel of hair and further incorporation of a higher alcohol such as cetanol or an oil to improve efficacy feeling. However, these hair cosmetics cannot be said to give smooth feel and moist feel to hair, and are known to be insufficient in reducing irritation to hair, scalp or skin.

It was found in recent years that a specific amideamine compound or its acid salt can confer smooth feel and softness on hair, and hair cosmetics compounded with the amideamine compound or its acid salt have been proposed (JP-A 5-271035, JP-A 9-71515, JP-A 2000-53537, Japanese Patent Application National Publication (Laid-Open) No. 2000-501430, JP-A 2001-342116, Japanese Patent Application National Publication (Laid-Open) No. 2002-500173, and JP-A 2003-183136). The amideamine compound or its salt is also known to provide hair cosmetics which are highly safe and show a mild action on skin etc. (JP-A 11-79947, FRAGRANSE JOURNAL, 24(12), 106-111 (1996)). As the specific amideamine, stearic acid dimethyl aminopropyl amide is widely known. WO-A 2004-030646 discloses a hair conditioner comprising 3 kinds of silicone, an amideamine, an acid, an aliphatic compound and an aqueous medium.

SUMMARY OF THE INVENTION

The present invention provides a hair cosmetic composition comprising the following components (a) and (b):

(a) an amideamine represented by the formula (I) (referred to hereinafter as amideamine (I)):

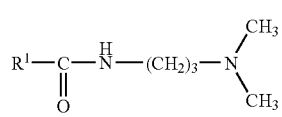

(I)

wherein $R^1CO$ represents aliphatic acid residues among which C20 or more aliphatic acid residues account for 60 wt % or more, C20 aliphatic acid residues account for 3 wt % or more, and C22 aliphatic acid residues account for 50 to 95 wt %, and (b) an aliphatic alcohol represented by the formula (II) (referred to hereinafter as aliphatic alcohol (II)):

(II)

wherein $R^2$ represents C8 to C30 saturated or unsaturated aliphatic hydrocarbon groups wherein linear aliphatic hydrocarbon groups account for 80 wt % or more.

The present invention also provides use of the above composition in hair-cosmetics.

DETAILED DESCRIPTION OF THE INVENTION

The conventional amideamine is problematic in gel formability upon incorporation of a higher alcohol or oil into it, and is not satisfactory in respect of smooth feel and moist feel conferred on hair.

The present invention provides hair cosmetics which are excellent in thickening property (gel formability) and stability with time, can confer sufficient smooth feel and moist feel during application to hair, washing and rinsing and sufficient smoothness and good combing after drying, and exhibit a mild action on skin etc. with high safety.

The present inventors found that, when a specific amideamine is selected from amideamines and used in combination with an alcohol containing a linear higher alcohol in a specific ratio, the resulting hair cosmetics can be rendered excellent in thickening property (gel formability) and stability with time, to confer sufficient smooth feel and moist feel during application to hair, washing and rinsing and sufficient smoothness and good combing after drying.

The hair cosmetics of the present invention are excellent in thickening property (gel formability) and stability with time, and can confer sufficient smooth feel and moist feel during application to hair, washing and rinsing and sufficient smoothness and good combing after drying. Further, the hair cosmetics exhibit a mild action on skin etc. with high safety.

In the aliphatic acid residues represented by $R^1CO$ in the amideamine (I) as the component (a) used in the present invention, C20 or more aliphatic acid residues account for 60 wt % or more, preferably 75 wt % or more, still more preferably 80 wt % or more, further more preferably 90 wt % or more, C20 aliphatic acid residues account for 3 wt % or more, preferably 4 wt % or more, still more preferably 5 wt % or more, and C22 aliphatic acid residues account for 50 to 95 wt %, preferably 55 to 95 wt %, still more preferably 70 to 95 wt %, still more preferably 80 to 95 wt %. In the present invention, the aliphatic residues mean the $R^1CO$ site.

In the aliphatic alcohol (II) as the component (b) in the present invention, $R^2$ represents C8 to C30 saturated or unsaturated aliphatic hydrocarbon groups wherein linear aliphatic hydrocarbon groups account for 80 wt % or more, preferably 85 wt % or more, still more preferably 90 wt % or more. The linear aliphatic hydrocarbon group is preferably a C8 to C30 linear alkyl or alkenyl group, more preferably a C10 to C26 linear alkyl group. The aliphatic alcohol (II) includes, for example, cetyl alcohol, stearyl alcohol, behenyl alcohol etc.

When the aliphatic alcohol (II) having such a degree of linear chain is used in combination with the amideamine (I) as the component (a) in the present invention, the resulting hair cosmetics can exhibit preferable viscosity, smoothness, and wet feel during moistening.

From the viewpoint of giving excellent feel to hair and for the stability of the product, the content of the component (a) in the hair cosmetics of the present invention is preferably 0.1 to 15 wt %, more preferably 0.5 to 10 wt %, still more preferably 0.5 to 5 wt %. The content of the component (b) is preferably 0.5 to 15 wt %, more preferably 1 to 10 wt %.

The hair cosmetics of the present invention preferably contain an organic acid (referred to hereinafter as component (c)) to further improve thickening property (gel formability) and stability with time.

The component (c) is preferably a C10 or less organic acid, and examples include acids having a C10 or less short alkyl group, such as alkyl phosphoric acid, alkyl sulfonic acid, alkyl sulfuric acid etc.; acidic amino acids such as L-glutamic acid, L-aspartic acid etc.; pyroglutamic acid; aromatic acids such as benzoic acid, p-toluene sulfonic acid etc.; hydroxy acids; and dicarboxylic acids. The hydroxy acids include hydroxy monocarboxylic acids such as glycolic acid, lactic acid, glyceric acid, gluconic acid, pantothenic acid etc.; hydroxy dicarboxylic acids such as malic acid, tartaric acid etc.; and hydroxy tricarboxylic acids such as citric acid etc. The dicarboxylic acids include oxalic acid, malonic acid, maleic acid, succinic acid, glutaric acid etc. From the viewpoint of retaining moisture and giving a softening effect to hair, hydroxy acids and pyroglutamic acid are particularly preferable, among which glycolic acid, lactic acid, malic acid and pyroglutamic acid are more preferable.

When the component (c) is incorporated into the hair cosmetics of the present invention, the components (a) and (c) may be compounded separately or may be compounded after an acid salt of amideamine (I) is previously formed. The amount of the component (c) incorporated is preferably 0.3 to 10 moles, more preferably 0.5 to 5 moles, per mole of the component (a).

The hair cosmetics of the present invention are used after partial or complete conversion to a salt by regulating pH in the composition, and used preferably at a pH of 2 to 8, more preferably at a pH of 3 to 6, from the viewpoint of good feel of hair and stability of the product.

In the hair cosmetics of the present invention, an aromatic alcohol is preferably incorporated from the viewpoint of improving smoothness and smooth feel during application/rinsing and conferring softness on hair after drying. The aromatic alcohol includes benzyl alcohol, phenethyl alcohol, phenoxy ethanol, benzyloxy ethanol etc. These aromatic alcohols may be used as a mixture of two or more thereof, and the content thereof is preferably 0.1 to 20.0 wt %, more preferably 0.1 to 5.0 wt %, from the viewpoint of conferring adsorptivity on the agent and elasticity on hair.

For the purpose of conferring moist feel and gathering feel on hair after drying and repairing damaged hair by restoration of the original lustrous vivid color of hair, a component having a hair restoration effect (referred to hereinafter as hair restoration component) is preferably incorporated. The hair restoration component includes amino acids, amino acid derivatives, vitamins, sphingosines, ceramides etc.

The amino acids include arginine, lysine, histidine, proline, cysteine, methionine, serine, threonine, tyrosine, glutamine, isoleucine etc. Arginine and lysine are particularly preferable.

The amino acid derivatives include trimethyl glycine, peptides such as dipeptides and tripeptides, acylated amino acids, acylalkyl amino acids etc. The amino acid derivatives also include animal-derived proteins such as keratin, elastin, collagen, lactoferrin, casein, α(β)-lactoalbumin, globulins, ovalbumin etc. or hydrolysates thereof, vegetable-derived proteins such as wheat, malt, soybean, silk etc. or hydrolysates thereof. In particular, keratin, elastin, collagen, casein and hydrolysates thereof, wheat protein, soybean protein, silk protein and hydrolysates thereof are preferable.

In the present invention, these amino acids and amino acid derivatives can be used alone or as a mixture of two or more thereof. The content thereof in the total amount of the hair cosmetics of the present invention is 0.01 to 7.0 wt %, more preferably 0.05 to 2.0 wt %.

The vitamins include tocopherol acetate, ascorbic acid, vitamin B1, vitamin B5, vitamin D, vitamin A, nicotinic acid amide, pantenol, pentothenyl ethyl ether etc., among which tocopherol acetate, pentenol, and pantothenyl ethyl ether are preferable. When the vitamins are contained, the amount of the vitamins compounded is preferably 0.01 to 2.0 wt %, more preferably 0.05 to 1.0 wt %, based on the total amount of the hair cosmetics of the present invention.

The sphingosines include dihydrosphingosine, phytosphingosine etc. The ceramides include N-acylated sphingosines, N-acylated phytosphingosines, N-acylated dihydrosphingosines etc. obtained by synthesis or extraction from naturally occurring materials. An acyl-substituted substituent group on sphingosine, dihydrosphingosine or phytosphingosine is a C8 to C22 linear or branched alkyl or alkenyl group, and 1 to 5 hydrogen atoms of the alkyl or alkenyl group may be substituted with hydroxyl groups. For example, it is possible to use not only ceramide 1, ceramide 2, ceramide 3, ceramide 1A, ceramide 6II, hydroxy caproyl phytosphingosine, but also synthetic pseudo-ceramides such as sphingolipid EX (JP-A 11-209248) and sphingolipid E (JP-B 01-042934). At least one kind of the sphingosines and ceramides can be used, and the content thereof is 0.01 to 5 wt %, more preferably 0.05 to 2 wt %, still more preferably 0.1 to 1 wt %, based on the whole composition.

For the purpose of improving hair protective effects such as conferment of smoothness, softness or luster on hair after drying, a silicone component is preferably incorporated into the hair cosmetics of the present invention. The silicone component includes silicone rubber, silicone oil, functional group-modified silicone etc., and can be exemplified by, for example, the following (A) to (H):

(A) Dimethyl Polysiloxane Oil

The dimethyl polysiloxane represented by the formula (III) is preferable, and for example, SH200C series, 1 cs, 50 cs, 200 cs, 1000 cs, 5000 cs (manufactured by Dow Corning Toray Silicone Co., Ltd.) etc. can be mentioned.

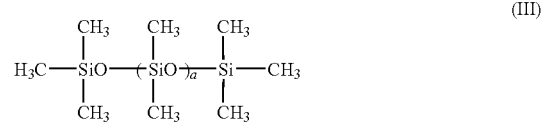

(III)

wherein a is an integer of 0 to 650.

(B) Highly Polymerized Dimethyl Polysiloxane

For example, BY11-026, BY22-19 (manufactured by Dow Corning Toray Silicone Co., Ltd.), FZ-3125 (manufactured by Nippon Unicar Company Limited) etc. may be mentioned.

When the highly polymerized dimethyl polysiloxane is incorporated into the hair cosmetics of the present invention, it is preferable that the highly polymerized dimethyl polysiloxane is dissolved in liquid oil and incorporated, or a dispersion thereof prepared in an aqueous solution of a cationic surfactant such as an acid salt of amideamine (I) or in an aqueous solution of a nonionic surfactant such as polyoxyethylene alkyl ether is incorporated. The liquid oil includes the dimethyl polysiloxane oil (A) described above and cyclic silicone (E) below or isoparaffin hydrocarbons.

(C) Amino-modified Silicone

The amino-modified silicone represented by the formula (IV) is preferable, and for example SS-3551 (manufactured by Nippon Unicar Company Limited), SF8452C (manufactured by Dow Corning Toray Silicone Co., Ltd.) etc. can be mentioned.

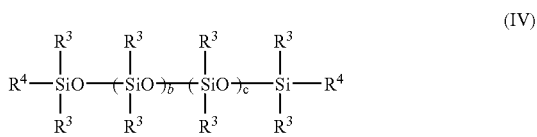
(IV)

wherein R³ represents a methyl group, R⁴ represents the same group as that of R⁵, a methyl group or a hydroxyl group, R⁵ represents a reactive functional group represented by —R⁶-Z whereupon R⁶ represents a C3 to C6 divalent hydrocarbon group, and Z represents a primary to tertiary amino-containing group or an ammonium-containing group, and b and c each represent a positive number, b+c is a number depending on the molecular weight, and the average molecular weight is preferably 3000 to 100000.

When the amino-modified silicone is used as an aqueous emulsion, the amount of the amino-modified silicone in the aqueous emulsion is preferably 20 to 60 wt %, more preferably 30 to 50 wt %. The aqueous emulsion of the amino-modified silicone is preferably SM8704C (manufactured by Dow Corning Toray Silicone Co., Ltd.) or the like.

(D) Polyether-Modified Silicone

For example, SH3771M (manufactured by Dow Corning Toray Silicone Co., Ltd.), SILSOFT A-843 and SILSOFT SHINE (both manufactured by Nippon Unicar Company Limited) etc. can be mentioned.

(E) Cyclic Silicone

For example, SH244 and SH245 (both manufactured by Dow Corning Toray Silicone Co., Ltd.) etc. can be mentioned.

(F) Fluorine-modified Silicone (G) Alkyl-modified Silicone (H) Amino-modified Siloxane/Polyoxyalkylene Block Copolymer The copolymer represented by the formula (V) is preferable, and for example FZ-3789 (manufactured by Nippon Unicar Company Limited) can be mentioned.

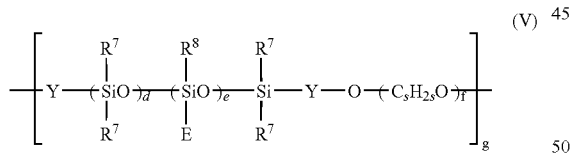
(V)

wherein R⁷ represents a hydrogen atom or a C1 to C6 monovalent hydrocarbon group, R⁸ represents either R⁷ or E, E represents a reactive functional group represented by —R⁹-Z whereupon R⁹ represents a direct bond or a C1 to C20 divalent hydrocarbon group, and Z represents a primary to tertiary amino-containing group or an ammonium-containing group, d represents a number of 2 or more, e represents a number of 1 or more, s represents a number of 2 to 10, s whose number is f may be the same or different, f represents a number of 4 or more, g represents a number of 2 or more, and Y represents a divalent organic group bound via a carbon-silicon atom to the adjacent silicon atom and bound via an oxygen atom to a polyoxyalkylene block chain, and a plurality of R⁷, R⁸ and E may be the same as or different from one another.

Among these silicone compounds, the dimethyl polysiloxane oil (A), the highly polymerized dimethyl polysiloxane (B), the cyclic silicone (E) or a mixture thereof, the amino-modified silicone (C) and the amino-modified siloxane/polyoxyalkylene block copolymer (H) are preferable, among which the amino-modified silicone (C) and the amino-modified siloxane/polyoxyalkylene block copolymer (H) are particularly preferable.

The content of the silicone component in the hair cosmetics of the present invention can be suitably determined in consideration of other components so as to give excellent feel to hair. Generally, the content of the silicone component is preferably 0.05 to 15.0 wt %, more preferably 0.1 to 10.0 wt %, still more preferably 0.1 to 5.0 wt %, from the viewpoint of sufficiently exhibiting the effect of the present invention, giving excellent feel for use and preventing friction during rinsing.

Depending on the object, other components generally used in hair cosmetics can be incorporated into the hair cosmetics of the present invention. Specific examples include cationic surfactants such as behenyl trimethyl ammonium chloride, stearyl trimethyl ammonium chloride, cetyl trimethyl ammonium chloride etc.; nonionic surfactants such as polyoxyethylene alkyl ether, polyoxyethylene sorbitan fatty ester, glycerin fatty ester, polyoxyethylene hardened castor oil etc.; polymer compounds such as cationized cellulose, hydroxylated cellulose, highly polymerized polyethylene oxide etc.; humectants such as glycerin, propylene glycol, dipropylene glycol etc.; higher fatty acids such as stearic acid, behenic acid, oleic acid etc.; ester oils such as isopropyl myristate; hydrocarbons such as liquid isoparaffin, Vaseline, squwalane etc.; anti-dandruff agents such as zinc pyrithion, benzalkonium chloride etc.; and other components such as a pealing agent, a solvent, a liquid crystal forming agent, a chelating agent, an UV absorber, an antioxidant, a preservative, a coloring agent, a perfume etc.

The hair cosmetics of the present invention can be used in the desired form of an aqueous solution, an ethanol solution, an emulsion, a suspension, gel, liquid crystals, aerosol etc.

The hair cosmetics of the present invention can be used in a hair rinse, hair conditioner, hair treatment, hair pack, hair cream, leave-on-treatment etc.

EXAMPLES

The present invention is described in more detail by reference to the Examples. The Examples illustrate the present invention and are not intended to limit the present invention.

Hereinafter, the term "%" refers to % by weight.

Examples 1 to 8 and Comparative Examples 1 to 3

Hair cosmetics (hair conditioners) having the compositions shown in Table 1 were prepared in the following manner and subjected to sensory evaluation in the following manner. The results are shown in Table 1.

<Preparation Method>

1) Ion exchange water and components other than the acid were introduced in predetermined amounts into a 100-ml beaker such that the amount of the final product became 300 g, and the components were then heated to 65° C. and uniformly dissolved.

2) Ion exchange water and the acid were introduced in predetermined amounts into a 500-ml beaker such that the amount of the final product became 300 g, and the acid was then heated to 65° C. and blended with the mixture obtained in 1) to prepare a hair conditioner.

<Sensory Evaluation Test>

While a bundle of hair (20 g, 20 cm, Japanese female hair once permed) was treated in the following manner, performance during application to the hair, during rinsing and after drying was evaluated sensorily by a panel of 5 persons.

3 g shampoo was used to wash the hair bundle. This shampoo composition contained 15% polyoxyethylene (C12) alkyl ether sodium sulfate (number of ethylene oxide units on average: 2.5) and 3% diethanol amide, the balance being water. Thereafter, 2 g of the prepared hair conditioner was applied to the hair, and the hair during application was evaluated. The hair was rinsed for about 30 seconds with running water at about 40° C., and the hair during rinsing was evaluated, then dried with a towel, and dried with a dryer, and after drying, the hair was evaluated. The easiness of spreading, smoothness and softness during application, smoothness and softness during rinsing, and easiness of combing after drying, and finishing feel were evaluated sensorily under the following criteria:

TABLE 2

|  |  | Example | Comparative example |  |
|---|---|---|---|---|
|  |  | 9 | 4 | 5 |
| Hair cosmetics (%) | Behenic acid dimethyl aminopropyl amide | 1.8 |  | 1.6 |
|  | Arachic acid dimethyl aminopropyl amide | 0.1 |  |  |
|  | Stearic acid dimethyl aminopropyl amide | 0.1 | 2 | 0.4 |
|  | Cetyl alcohol | 0.5 | 0.5 | 0.5 |
|  | Stearyl alcohol | 4 | 4 | 4 |
|  | Behenyl alcohol | 0.5 | 0.5 | 0.5 |
|  | Lactic acid | 0.6 | 0.7 | 0.6 |
|  | Ion exchange water | Balance | Balance | Balance |
|  | Propylene glycol | 0.5 | 0.5 | 0.5 |
| Viscosity | 1 day after preparation [mPa·s] | 8900 | 400 | 650 |
|  | 1 month after preparation [mPa·s] | 9100 | 1200 | 2000 |

TABLE 1

|  |  | Example |  |  |  |  |  |  |  | Comparative example |  |  |
|---|---|---|---|---|---|---|---|---|---|---|---|---|
|  |  | 1 | 2 | 3 | 4 | 5 | 6 | 7 | 8 | 1 | 2 | 3 |
| Hair cosmetics (%) | Behenic acid dimethyl aminopropyl amide | 1.8 | 1.8 | 1.8 | 1.8 | 1.8 | 1.8 | 1.8 | 1.6 |  | 1.6 | 2 |
|  | Arachic acid dimethyl aminopropyl amide | 0.1 | 0.1 | 0.1 | 0.1 | 0.1 | 0.1 | 0.1 | 0.4 |  |  |  |
|  | Stearic acid dimethyl aminopropyl amide | 0.1 | 0.1 | 0.1 | 0.1 | 0.1 | 0.1 | 0.1 |  | 2 | 0.4 |  |
|  | Stearyl alcohol | 4 | 4 | 4 | 4 | 4 | 4 | 4 | 4 | 4 | 4 | 4 |
|  | Lactic acid | 0.6 | 0.6 | 0.6 | 0.6 | 0.6 |  |  | 0.6 | 0.7 | 0.6 | 0.6 |
|  | L-glutamic acid |  |  |  |  |  | 0.7 | 0.7 |  |  |  |  |
|  | benzyl oxyethanol |  | 0.3 |  | 0.3 |  |  | 0.3 |  |  |  |  |
|  | Benzyl alcohol |  |  | 0.3 |  | 0.3 |  |  |  |  |  |  |
|  | Dimethyl polysiloxane*1 |  |  |  | 2.0 | 2.0 |  |  |  |  |  |  |
|  | Arginine |  |  |  |  | 0.2 |  |  |  |  |  |  |
|  | Acetate tocopherol |  |  |  |  | 0.1 |  |  |  |  |  |  |
|  | Oleic acid monoglyceride |  |  |  | 0.2 | 0.2 |  |  |  |  |  |  |
|  | Ion exchange water | Balance | Balance | Balance | Balance | Balance | Balance | Balance | Balance | Balance | Balance | Balance |
|  | Propylene glycol | 0.5 | 0.5 | 0.5 | 0.5 | 0.5 | 0.5 | 0.5 | 0.5 | 0.5 | 0.5 | 0.5 |
| Result of sensory evaluation | During application | Easiness in spreading | A | A | A | A | A | A | A | B | B | B | B |
|  |  | Smoothness | A | A | A | A | A | B | A | A | B | B | B |
|  |  | Softness | B | A | A | A | A | B | A | B | B | B | C |
|  | during rinsing | Smoothness | A | A | A | A | A | B | B | A | C | C | B |
|  |  | Softness | B | A | A | A | A | B | A | B | B | B | B |
|  | After drying | Easiness in combing | B | B | B | A | A | B | B | B | B | B | B |
|  |  | Finishing feeling | B | B | B | A | A | B | B | B | B | B | C |

*1: BY25-320 manufactured by Dow Corning Toray Silicone Co., Ltd.
A: Reported to be effective by 4 or more persons.
B: Reported to be effective by 3 persons.
C: Reported to be effective by 2 persons.
D: Reported to be effective by 1 or less person.

Example 9 and Comparative Examples 4 to 5

Hair cosmetics (hair conditioners) having the compositions shown in Table 2 were prepared in the same manner as in Example 1, and the viscosity of the hair cosmetics 1 day and 1 month (storage at 25° C.) after the preparation were measured at 30° C. by viscometer TV-10 manufactured by Toki Sangyo Co., Ltd. The results are shown in Table 2.

As can be seen from the results in Table 2, the increase in viscosity with time is more suppressed in the Example of the present invention than in the Comparative Examples.

Examples 10 to 15

Hair cosmetics (hair conditioners) having the compositions shown in Table 3 were prepared in the same manner as in Example 1, and hair bundles were treated with the hair cosmetics in the same manner as in Example 1, and the finishing feel, moist feel, smooth feel, softness and luster were evaluated sensorily by a panel of 5 persons under the same criteria as in Example 1. The results are shown in Table 3.

TABLE 3

|  |  | Example | | | | | |
| --- | --- | --- | --- | --- | --- | --- | --- |
|  |  | 10 | 11 | 12 | 13 | 14 | 15 |
| Hair cosmetics (%) | Behenic acid dimethyl aminopropyl amide | 1.8 | 1.8 | 1.8 | 1.8 | 1.8 | 1.8 |
|  | Arachic acid dimethyl aminopropyl amide | 0.1 | 0.1 | 0.1 | 0.1 | 0.1 | 0.1 |
|  | Stearic acid dimethyl aminopropyl amide | 0.1 | 0.1 | 0.1 | 0.1 | 0.1 | 0.1 |
|  | Stearyl alcohol | 6 | 6 | 6 | 6 | 6 | 6 |
|  | Lactic acid | 0.6 | 0.6 | 0.6 | 0.6 | 0.6 | 0.6 |
|  | Benzyloxy ethanol | 0.5 | 0.5 | 0.5 | 0.5 | 0.5 | 0.5 |
|  | Dimethyl polysiloxane*[1] |  | 2.0 | 2.0 | 2.0 | 2.0 | 2.0 |
|  | Arginine |  | 0.2 |  |  |  |  |
|  | Keratin hydrolysates*[2] |  |  | 0.2 |  |  |  |
|  | Penthenyl ethyl ether |  |  |  | 0.2 |  |  |
|  | Synthetic pseudo-ceramide 1*[3] |  |  |  |  | 0.2 |  |
|  | Synthetic pseudo-ceramide 2*[4] |  |  |  |  |  | 0.1 |
|  | Amino-modified silicone*[5] |  | 0.5 | 0.5 | 0.5 | 0.5 | 0.5 |
|  | Ion exchange water | Balance | Balance | Balance | Balance | Balance | Balance |
|  | Propylene glycol | 0.5 | 0.5 | 0.5 | 0.5 | 0.5 | 0.5 |
| Result of sensory evaluation | After drying Finishing feel | B | A | A | A | A | A |
|  | Moist feel | B | B | A | B | A | A |
|  | Smooth feel | B | A | B | B | A | A |
|  | Softness | B | B | B | A | B | B |
|  | Gloss | B | A | AA | A | B | B |

*[1]: BY25-320 manufactured by Dow Corning Toray Silicone Co., Ltd.
*[2]: Promoist WK-H manufactured by Seiwa Kasei
*[3]: Sofcareceramide SL-E manufactured by Kao Corporation
*[4]: N-stearolyl sphingosine munufactured by Wako Pure Chemicals
*[5]: FZ-2789 manufactured by Nippon Unicar Company Limited Examples 16 and 17 and Comparative Examples 6 to 8

Hair cosmetics (hair conditioners) having the compositions shown in Table 4 were prepared in the same manner as in Example 1 and then left for one day, and hair bundles were treated with the hair cosmetics in the same manner as in Example 1, and the state during application, during rinsing and after drying was evaluated sensorily by a panel of 5 persons under the same criteria as in Example 1. The results are shown in Table 4.

As can be seen from the results in Table 4, an excellent effect during application, during rinsing and after drying can be exhibited by blending the aliphatic alcohol (II) as the component (b) in the present invention.

Comparative Example 9

A hair cosmetic (hair conditioner) was prepared in the same manner with the same composition as in Example 1 except that Incromine BB manufactured by CRODA was used, and the hair conditioner was evaluated sensorily under the same criteria as in Example 1. The composition of fatty acid residues of Incromine BB manufactured by CRODA was that $C_{15}H_{31}CO/C_{17}H_{35}CO/C_{19}H_{39}CO/C_{21}H_{43}CO/C_{23}H_{47}CO$ was 2/24/11/62/1. Results of this conditioner were as follows: easiness in spreading, B; smoothness, B; softness, B; smoothness during rinsing, B; softness during rinsing, B; easiness in combing after drying, B; and finishing feel, B.

TABLE 4

|  |  | Example | | Comparative example | | | |
| --- | --- | --- | --- | --- | --- | --- | --- |
|  |  | 16 | 17 | 6 | 7 | 8 | 9 |
| Hair cosmetics (%) | Behenic acid dimethyl aminopropyl amide | 2.25 | 2.25 | 2.25 | 2.25 | 2.25 |  |
|  | Arachic acid dimethyl aminopropyl amide | 0.13 | 0.13 | 0.13 | 0.13 | 0.13 |  |
|  | Stearic acid dimethyl aminopropyl amide | 0.12 | 0.12 | 0.12 | 0.12 | 0.12 |  |
|  | Incromine BB |  |  |  |  |  | 2.0 |
|  | Stearyl alcohol | 6.5 | 5.85 | 5 | 4.23 | 3.25 | 4 |
|  | 2-octyl-1-dodecanol |  | 0.65 | 1.5 | 2.28 | 3.25 |  |
|  | L-glutamic acid | 0.8 | 0.8 | 0.8 | 0.8 | 0.8 |  |
|  | Lactic acid |  |  |  |  |  | 0.6 |
|  | Ion exchange water | Balance | Balance | Balance | Balance | Balance | Balance |
|  | Propylene glycol | 0.5 | 0.5 | 0.5 | 0.5 | 0.5 | 0.5 |

TABLE 4-continued

|  |  |  | Example | | Comparative example | | | |
|---|---|---|---|---|---|---|---|---|
|  |  |  | 16 | 17 | 6 | 7 | 8 | 9 |
| Result of sensory evaluation | During application tion | Easiness in spreading | A | A | B | B | C | B |
|  |  | Smoothness | A | B | B | C | C | B |
|  |  | Softness | B | B | B | C | C | B |
|  | during rinsing | Smoothness | A | A | B | C | C | B |
|  |  | Softness | B | B | B | C | C | B |
|  | After drying | Easiness in combing | B | B | B | A | A | B |
|  |  | Finishing feel | B | B | B | A | A | B |

Example 18

As the amideamine (I), the amideamine represented by formula (A) below [purity 99.6% (other components: unreacted aliphatic acid, unreacted amine, water etc.)] (referred to hereinafter as amideamine A) synthesized from LUNAC BA (Kao Corporation) and dimethyl amino propyl amine was used to prepare a conditioner having the following composition. This conditioner was excellent in rich feeling and its durability during application and rinsing, and in softness, smoothness, and smooth feel and combing feel after drying.

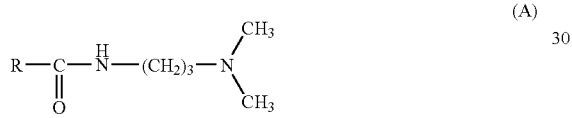

(A)

wherein the composition of RCO is $C_{17}H_{35}CO/C_{19}H_{39}CO/C_{21}H_{43}CO/C_{23}H_{47}CO=1\%/9\%/88\%/2\%$.

<Conditioner Composition>

| Amideamine A | 1.5% |
|---|---|
| Stearyl alcohol*1 | 4.0% |
| Glycerin | 1.0% |
| Benzyloxy ethanol | 0.3% |
| Siliccone*2 | 2.0% |
| Amino-modifed siloxane/polyoxyalkylene block copolymer*3 | 0.5% |
| Lactic acid | 0.5% |
| Dipentaerythritol fatty ester*4 | 0.2% |
| Hydroxyethyl cellulose*5 | 0.2% |
| Highly polymerized polyethylene glycol*6 | 0.05% |
| Acetate tocopherol | 0.1% |
| Perfume, methyl paraben | suitable amount |
| Purified water | balance |
| (pH 4.5) |  |

*1CALCOL 8098 manufactured by Kao Corporation
*2BY00-003 manufactured by Dow Corning Toray Silicone Co., Ltd.
*3FZ-2789 manufactured by Nippon Unicar Company Limited
*4Cosmol 168AR manufactured bby The Nisshin OilliO Group, Ltd.
*5SE-850 manufactured by Daicel Chemical Industries, Ltd.
*6Polyox WSRN-60K manufactured by Union Carbide.

Example 19

A conditioner having the following composition was prepared. This conditioner was excellent in rich feel and its durability during application and rinsing and in softness, smoothness, and soft feel and combing after drying.

<Treatment Composition>

| Amideamine A | 2.0% |
|---|---|
| Behenyl trimethyl ammonium chloride | 0.3% |
| Stearyl alcohol | 4.5% |
| Behenyl alcohol*1 | 1.5% |
| Isononyl isononate*2 | 0.5% |
| Silicone*3 | 1.0% |
| Amino-modified silicone*4 | 0.5% |
| Glycolic acid | 0.5% |
| Malic acid | 0.1% |
| Dipropylene glycol | 3.0% |
| Benzyl alcohol | 0.3% |
| Arginine | 0.2% |
| Pantothenyl ethyl ester | 0.1% |
| Perfume, methyl paraben | suitable amount |
| Purified water | balance |
| (pH 4.0) |  |

*1CALCOL 222080 manufactured by Kao Corporation
*2Salacos 99 manufactured bny The Nisshin OilliO Group, Ltd.
*3SH200C-5000cs manufactured by Dow Corning Toray Silicone Co., Ltd.
*4SM8704C manufactured by Dow Corning Toray SIlicone Co., Ltd.

Example 20

A conditioner having the following composition was prepared. This conditioner was excellent in rich feel and its durability during application and rinsing and in softness, smoothness, and soft feel and combing after drying.

<Conditioner Composition>

| Amideamine A | 1.5% |
|---|---|
| Stearyl alcohol*1 | 4.0% |
| Propylene glycol | 0.5% |
| Benzyloxy ethanol | 0.3% |
| Silicone*2 | 2.0% |
| Amino-modified siloxane/polyoxyalkylene block copolymer*3 | 0.5% |
| Lactic acid | 0.5% |
| Oleic acid glyceride | 0.2% |
| Ceramide 1*4 | 0.2% |
| Wheat protein hydrolysate*5 | 0.3% |
| Perfume, methyl paraben | suitable amount |
| Purified water | balance |
| (pH 4.5) |  |

*1CALCOL 8098 manufactured by Kao Corporation
*2BY00-003 manufactured by Dow CXorning Toray Silicone Co., Ltd.
*3FZ-3789 manufactured by Nippon Unicar Company Limited
*4Phytoceramide 1 manufactured by Gist-brocades/Cosmoferm
*5Promoist WG manufactured by Seiwa Kasei

The invention claimed is:

1. A hair cosmetic composition comprising the following components (a) and (b):
   (a) 0.1 to 15 wt. % of an amideamine represented by the formula (I):

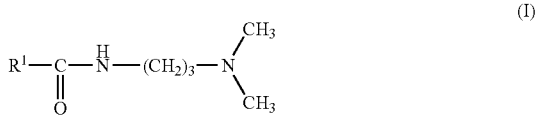

and a salt of said amideamine,
   wherein $R^1CO$ represents aliphatic acid residues among which C20 or more aliphatic acid residues account for 80 wt % or more, C20 aliphatic acid residues account for 3 wt % or more, and C22 aliphatic acid residues account for 70 to 95 wt %, and
   (b) 0.5 to 15 wt. % of an aliphatic alcohol component comprising at least one aliphatic alcohol selected from the group consisting of cetyl alcohol, stearyl alcohol and behenyl alcohol
   wherein linear aliphatic hydrocarbon groups account for 80 wt % or more to the total aliphatic hydrocarbon groups.

2. The composition according to claim 1, which further comprises (c) an organic acid.

3. The composition according to claim 2, wherein the organic acid is at least one member selected from the group consisting of hydroxy acids and pyroglutamic acid.

4. The composition according to claim 1, which further comprises an aromatic alcohol.

5. The composition according to claim 1, which further comprises a component having a hair repair effect.

6. The composition according to claim 1, wherein the component having a hair repair effect is at least one member selected from the group consisting of amino acids, amino acid derivatives, vitamins, sphingosines and ceramides.

7. The composition according to claim 1, which further comprises a silicone component.

8. A method of treating hair comprising applying to hair the composition of claim 1.

9. The hair cosmetic composition of claim 1, wherein said C22 aliphatic acid residue is from behenic acid.

10. The hair cosmetic composition of claim 1, wherein said C20 aliphatic acid residue is from arachic acid.

11. The hair cosmetic composition of claim 1, wherein said aliphatic alcohol is stearyl alcohol.

12. The hair cosmetic composition of claim 1, wherein said C20 aliphatic acid residue accounts for 5 wt. % or more.

13. The hair cosmetic composition of claim 2 wherein said organic acid is present in an amount of 0.3 to 10 moles per mole of component (a).

14. The hair cosmetic composition of claim 4 wherein said aromatic alcohol is present in amount of 0.1 to 20.0 wt. %.

15. The hair cosmetic composition of claim 1, wherein said composition has a pH of from 2 to 8.

16. The hair cosmetic composition of claim 1, wherein said composition has a pH of from 3 to 6.

17. The hair cosmetic composition of claim 6, wherein said component having a hair repair effect is an amino acid or an amino acid derivative which is present in an amount of 0.01 to 7.0 wt. %.

18. The hair cosmetic composition of claim 6, wherein said component having a hair repair effect is a vitamin which present in an amount of 0.01 to 2.0 wt. %.

19. The hair cosmetic composition of claim 7, wherein said silicone component is present in an amount of 0.05 to 15.0 wt. %.

20. The hair cosmetic composition of claim 1, wherein said C20 aliphatic acid residue accounts for 3 to 20 wt. %.

* * * * *

UNITED STATES PATENT AND TRADEMARK OFFICE
CERTIFICATE OF CORRECTION

PATENT NO. : 7,601,339 B2
APPLICATION NO. : 11/098528
DATED : October 13, 2009
INVENTOR(S) : Kaharu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1224 days.

Signed and Sealed this

Fifth Day of October, 2010

David J. Kappos
*Director of the United States Patent and Trademark Office*